United States Patent [19]
Sliman et al.

[11] Patent Number: 5,212,839
[45] Date of Patent: May 25, 1993

[54] DIAPER HOLDER FOR A PERSON IN A BODY CAST

[76] Inventors: John M. Sliman; Donna M. Sliman, both of Rt. 5 Box 984, Deridder, La. 70634

[21] Appl. No.: 858,745

[22] Filed: Mar. 27, 1992

[51] Int. Cl.⁵ .................. A41B 9/00; A61F 13/15
[52] U.S. Cl. .......................... 2/408; 2/312; 2/321; 604/395; 604/396; 604/400; 604/401
[58] Field of Search ............. 624/391, 393, 394, 395, 624/396, 397, 398, 399, 400, 401, 402; 2/311, 312, 313, 314, 318, 319, 321, 406, 408, 400402, 338

[56] References Cited

U.S. PATENT DOCUMENTS

| | | | |
|---|---|---|---|
| 881,130 | 3/1908 | Jordan | 604/401 X |
| 1,245,655 | 11/1917 | Allen . | |
| 2,798,489 | 7/1957 | Behrman | 604/401 X |
| 3,358,980 | 12/1967 | Rosenblatt | 604/391 |
| 3,554,196 | 1/1971 | Wargo | 604/402 |
| 3,765,401 | 10/1973 | Vass | 604/401 X |
| 4,022,212 | 5/1977 | Lovison | 604/396 X |
| 4,031,897 | 6/1977 | Graetz | 604/401 X |
| 4,145,763 | 3/1979 | Abrams et al. | 604/391 X |
| 4,932,079 | 6/1990 | Bridgewater | 2/313 |
| 4,932,950 | 6/1990 | Johnson | 604/393 X |
| 4,964,860 | 10/1990 | Gipson et al. | 604/391 |

FOREIGN PATENT DOCUMENTS

| | | | |
|---|---|---|---|
| 8800011 | 1/1988 | PCT Int'l Appl. | 2/311 |
| 1200177 | 7/1970 | United Kingdom | 604/397 |

Primary Examiner—Randall L. Green
Assistant Examiner—Mary Beth D. Jones
Attorney, Agent, or Firm—Edwin E. Greigg; Ronald E. Greigg

[57] ABSTRACT

A diaper holding device for a person in a body cast. The diaper holding device includes two T-shaped portions having VELCRO on a face surface so that the two T-shaped portions can surround the body cast with a portion between the legs of the body cast.

6 Claims, 2 Drawing Sheets

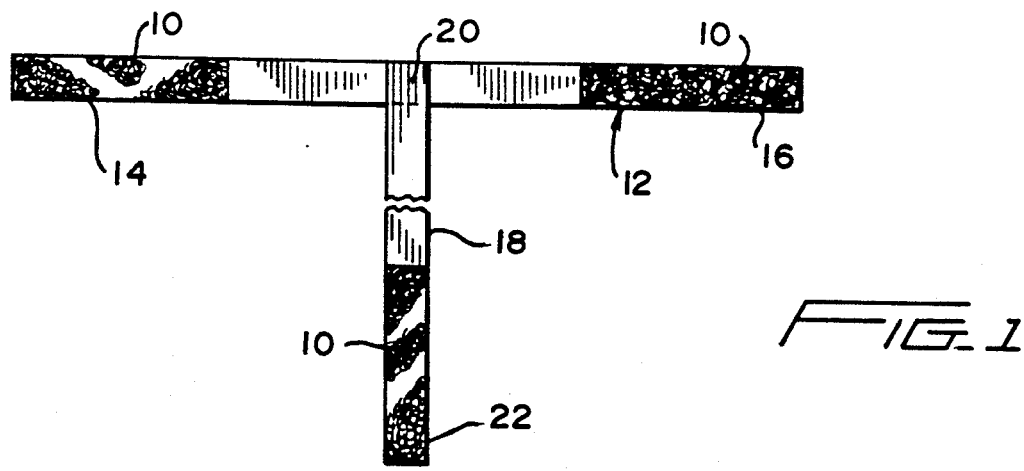
FIG_1
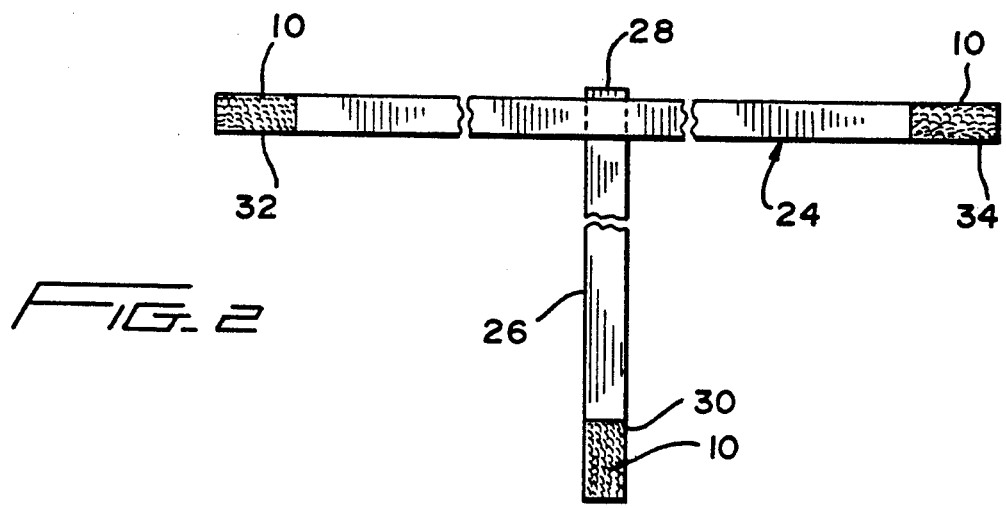
FIG_2
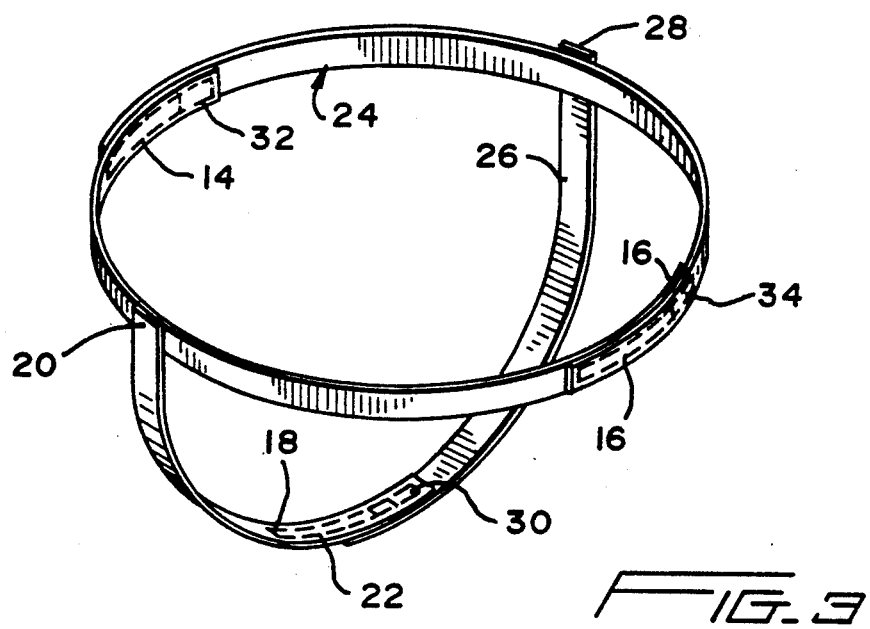
FIG_3

DIAPER HOLDER FOR A PERSON IN A BODY CAST

BACKGROUND OF THE INVENTION

This invention relates to an adjustable strap device for holding a diaper on a person in a body cast.

Heretofore a diaper for a person in a body cast has been held in place by tape secured at one end to the diaper and the opposite end of the tape secured to the body cast. Tapes as presently used do not remain taped in place especially the end secured to the body cast which is normally filled o plaster-of-paris.

Heretofore, various types of sanitary belts have been used for securing a sanitary napkin or bandages in place on a person's body. Such prior art devices are found in U.S. Pat. Nos. 1,245,655; 4,031,897; 4,932,950 and 4,964,860.

OBJECT AND SUMMARY OF THE INVENTION

The present invention has an advantage over the use of tape and fixed belt arrangements in that the device is not secured to the diaper but is affixed in place to hold the diaper in place.

It is therefore an object to provide an adjustable belt arrangement which is used to secure a diaper on a person in a body cast.

Another object is to provide an adjustable device by which one size fits all within a certain size spread.

Still another object is to provide a diaper securing device which is easily assembled and adjusted for proper size in holding a diaper in place on a person in a body cast.

Yet another object is to provide a diaper holding device for a person in a body cast which is easily adjustable and which may use buckles and/or VELCRO which will be comfortable and easy to adjust.

VELCRO is a synthetic material which adheres when pressed together and will be referred to as VELCRO throughout the disclosure.

Other objects and advantages will become obvious to those skilled in the art from a view of the attached drawing wherein:

BRIEF DESCRIPTION OF THE DRAWINGS

FIGS. 1 and 2 illustrate front and back T-straps which are secured together for holding a diaper in place on a body cast;

FIG. 3 illustrates the straps of FIGS. 1 and 2 assembled together as for use;

DETAILED DESCRIPTION

Figure 4:
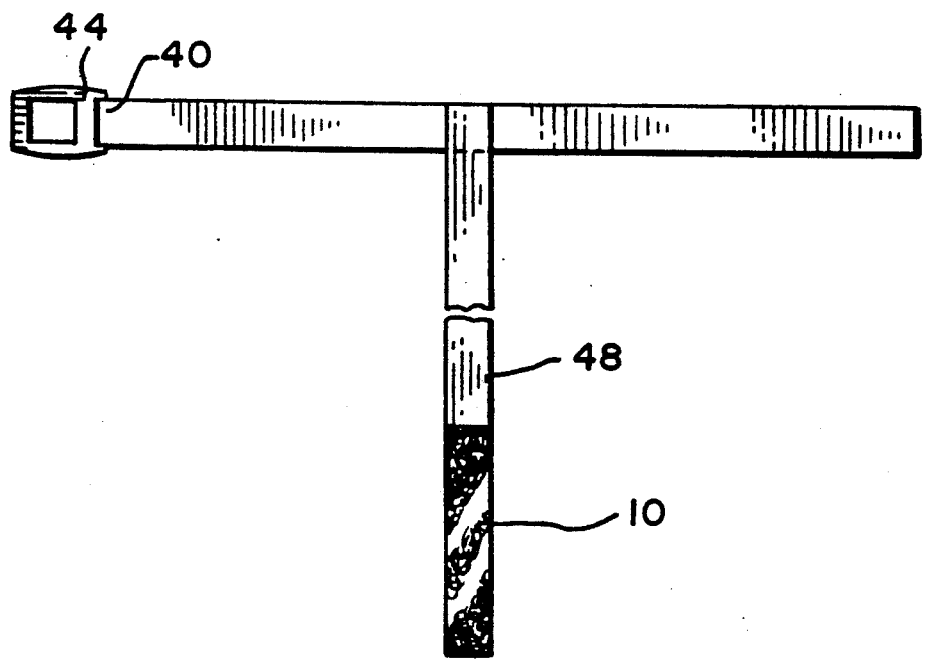
FIGS. 4 and 5 are modifications of the T-straps of FIGS. 1 and 2 in which one end of each of the T-straps that surround the body is provided with a buckle.

The diaper holding device includes two T-shaped straps or belts which are made of a non-extensible material such as leather, cloth, plastic or any other suitable flexible material and assembled together to form the diaper holding device for a person in a body cast. One T-shaped strap or belt is formed by a body piece 12 having opposite ends 14 and 16 which fits about one-half of the body and a crotch piece 18 which is secured at one end 20 to the body piece 12 at its mid-point and which includes a free end 22 that extends from the body piece 12 to between the legs of the person in a body cast. The other T-shaped strap or belt is substantially the same an includes a body piece 24 having ends 32 and 34 and a crotch piece 26 secured at one end 28 to the body piece and which has a free end 30 that extends between the legs of the person in the body cast. Each end of each of the body pieces 12 and 24 are equipped with VELCRO 10 so that the ends of the body pieces can be secured together to form a belt that encircles the body cast. The VELCRO will be applied on the faces of the body pieces starting at their loose ends such that the adjacent ends of each of the body piece will adhere to each other.

In order to prevent the VELCRO from being toward the body, one body piece 12 will have the VELCRO on a face surface away from the body when in use and extended along a long length of the body piece with the other body piece having the VELCRO of shorter length beginning at the loose end so that it will overlap at least a portion of the VELCRO of extended length. Also, the crotch pieces will of such that VELCRO extends along a long length of one piece on the face surface away from the body and the crotch strap face of the other piece will have VELCRO on only a short piece on a face surface toward the body so that the VELCRO on the one crotch piece will overlap the other piece without any VELCRO exposed toward the body.

As shown, the body piece 12 and crotch piece 18 in FIG. 1 can be used as the front piece so that the VELCRO 10 is away from the body. When the body piece 12 is placed on the body the end 16 will be on the left side, the end 14 will be on the right side and the crotch strap will extend toward the back side between the legs with the VELCRO away from the body. The body piece 24 and crotch piece 26 of FIG. 2 would be the back piece. Thus, the end 32 will be on the right side of the body, the end 34 will be on the left side of the body and the crotch piece 2 will extend between the legs toward the front with the VELCRO facing up. Thus, the short piece of VELCRO shown in FIG. 2 will overlap the VELCRO ends of the strap of FIG. 1 on the outside face thereof. The body pieces 12 and 24 could be reversed with the body piece 12 as the back and the body piece 24 used as the front. In this configuration, the body pieces as shown in FIGS. 1 and 2 would be reversed so that the VELCRO on the body piece 12 and crotch would be from the rear but on the outside face. Likewise, the body piece 24 and crotch shown in FIG. 2 could be reversed and be used as the front body piece. The important feature is that the exposed VELCRO not covered by the other strip should be on a face surface portion which is not toward the body. With one body strap having a long length of VELCRO thereon and the other body portion having only short layers of VELCRO thereon the body belts can be used to surround the body with adjustment for length. Likewise, the crotch straps would be adjustable for length.

One size fits all is to mean that the body pieces for a baby would be of a certain length that the body pieces for a youth would be another length; and that a body piece for an adult would be of still a different length.

The diaper support set forth herein can be used by unskilled as well as skilled persons. The two body portions can be used interchangeably for front and back provided the VELCRO surfaces are facing so that the VELCRO is not exposed to the body. The VELCRO crotch pieces afford one the opportunity to quickly disconnect and connect the crotch pieces for changing a diaper which is adjacent the body with the crotch pieces on the outside of the diaper.

Figure 5:
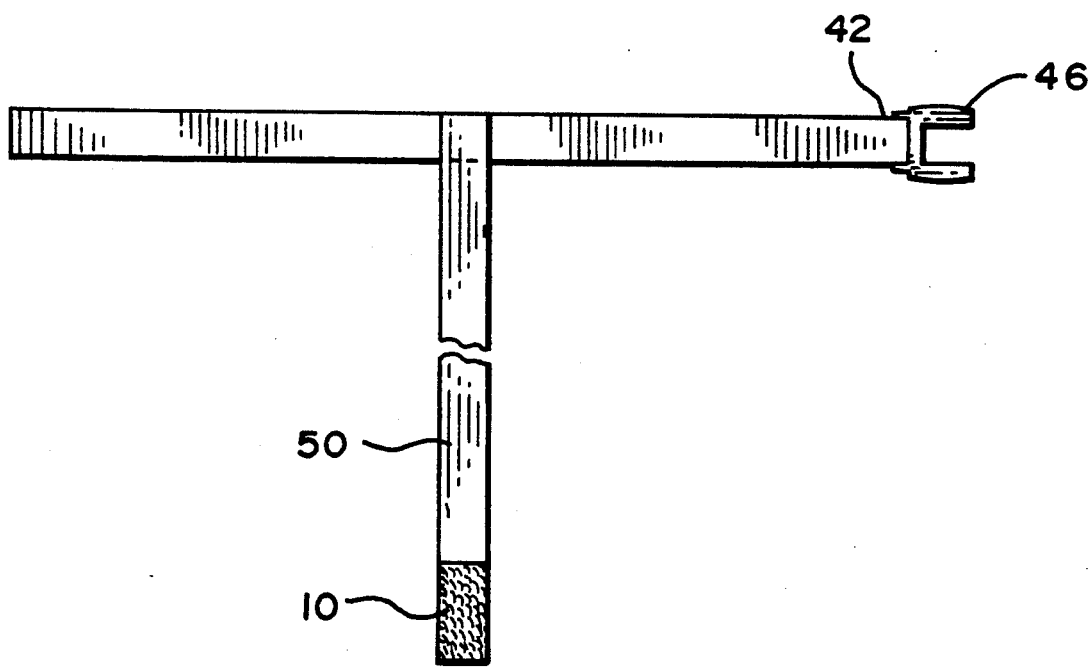

FIGS. 4 and 5 illustrate a modification of the body belt portions shown in FIGS. 1 and 2. As shown in FIGS. 4 and 5, one of the ends 40, 42 of the first and second body belt portions is provided with a buckle 44 and 46, respectively. The body belts are interchangeable such that the first or second body belt portions may be interchangeable for front and back use. The buckle end of each belt portion buckles to the end of the other belt portion which does not have a buckle but does have a mating end to form a complete body belt. The VELCRO ends then fit together to form the complete crotch portion. Therefore, the belt portions can be secured together and adjusted for different sized bodies. The crotch pieces 48 and 50 are provided with VELCRO. It will be obvious to one skilled in the art to provide long lengths of VELCRO and short lengths of VELCRO on either of the faces of the crotch portion 48, 50 so long as the VELCRO is not exposed to the body cast when in use. For ease of manufacture, the first and second body belt portions can be made the same with one end portion including the belt buckle, with the first and second body crotch portions provided with VELCRO. Obviously, one of the crotch portions could be made with a buckle so that the body portions and crotch portions would be buckled togegther.

The foregoing relates to a preferred exemplary embodiment of the invention, it being understood that other variants and embodiments thereof are possible within the spirit and scope of the invention, the latter being defined by the appended claims.

What is claimed and desired to be secured by Letters Patent of the United States is:

1. A diaper holder for a person in a body cast, which comprises a first narrow body belt portion having first and second opposite ends, said first narrow body belt portion includes VELCRO on one face extending for a length from said first and second opposite ends inwardly of said first and second opposite ends, a first narrow body crotch portion having a first end secured to said first narrow body belt portion approximately at a mid-point of the length of said first narrow body portion and a second end which is free of any connection to said first narrow body belt portion, said first narrow body crotch portion includes VELCRO on one face thereof which extends for a length from said second end toward said first end; a second narrow body belt portion having third and fourth opposite ends, said second narrow body belt portion includes VELCRO on one face thereof juxtaposed said third and fourth ends, a second narrow body crotch portion having a third end secured to said second body belt portion approximately at a mid-point of the length of said second narrow body portion and a fourth end which is free of any connection to said second narrow body portion; said second narrow body crotch portion includes VELCRO on one face thereof juxtaposed said fourth end thereof, said VELCRO on said first and second opposite ends of said first narrow body belt portion is on a face away from the body cast and extends for a greater length than said VELCRO on said third and fourth opposite ends of said second narrow body belt portion, whereby the VELCRO on the first and third opposite ends and VELCRO on said second and fourth opposite ends of said first and second narrow body belt portions are secured together to form a composite body belt and the VELCRO on said second and fourth ends of said first and second narrow crotch body portions are secured together to form a single crotch body portion.

2. A diaper holder as set forth in claim 11, in which, said first and second narrow body belt portions, and said first and second narrow crotch portions are formed of non-extensible material.

3. A diaper holder for a person in a body cast, which comprises a first narrow body belt portion having first and second opposite ends, a first narrow body crotch portion said first narrow body crotch portion having a first end secured to said first narrow body belt portion approximately at a mid-point of the length of said first narrow body portion and a second end which is free of any connection to said first narrow body belt portion, a second narrow body belt portion having third and fourth opposite ends, a second narrow body crotch portion having a third end secured to said second body belt portion approximately at a mid-point of the length of said second narrow body portion and a fourth end which is free of any connection to said second narrow body portion; one end of each of said first and second narrow body belt portions has a belt buckle thereon with the opposite end of each of said first and second narrow body belt portions being free of a belt buckle whereby the end of said first narrow body belt portion which is free of a belt buckle is secured to the belt buckle of the second narrow body belt portion and the free end of the body belt portion of the second narrow body belt is secured to the belt buckle of the first narrow body belt portion to form a composite body belt, said second end of said first narrow body crotch portion and said fourth end of said second narrow body crotch portion having means to secure each to the other to form a single crotch body portion.

4. A diaper holder as set forth in claim 3, in which, said first and second narrow body belt portions, and said first and second narrow crotch portions are formed of non-extensible material.

5. A diaper holder as set forth in claim 3, in which said means to secure said first and second narrow body crotch portions comprises VELCRO on their second and fourth ends respectively for connection to each other.

6. A diaper holder as set forth in claim 5, in which, said first and second narrow body belt portions, and said first and second narrow crotch portions are formed of non-extensible material.

* * * * *